(12) United States Patent
Bilitz (10) Patent No.: US 12,383,298 B2
(45) Date of Patent: Aug. 12, 2025

(54) DUAL-ACTION THROMBECTOMY CATHETER

(71) Applicant: KONINKLIJKE PHILIPS N.V., Eindhoven (NL)

(72) Inventor: Mark Bilitz, Plymouth, MN (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 378 days.

(21) Appl. No.: 17/911,683

(22) PCT Filed: Mar. 16, 2021

(86) PCT No.: PCT/EP2021/056611
§ 371 (c)(1),
(2) Date: Sep. 15, 2022

(87) PCT Pub. No.: WO2021/185799
PCT Pub. Date: Sep. 23, 2021

(65) Prior Publication Data
US 2023/0137662 A1 May 4, 2023

Related U.S. Application Data

(60) Provisional application No. 62/990,488, filed on Mar. 17, 2020.

(51) Int. Cl.
*A61B 17/3207* (2006.01)
*A61B 17/00* (2006.01)

(52) U.S. Cl.
CPC ............... *A61B 17/320758* (2013.01); *A61B 17/320783* (2013.01)

(58) Field of Classification Search
CPC ........ A61B 17/320758; A61B 17/3207; A61B 17/320783; A61B 2017/320775; A61B 2017/320733; A61B 2017/320766
See application file for complete search history.

(56) References Cited

U.S. PATENT DOCUMENTS

| 8,114,106 | B2 | 2/2012 | Straub |
| 8,920,450 | B2 | 12/2014 | Zeroni |
| 2006/0229646 | A1 | 10/2006 | Sparks |
| 2011/0152907 | A1 | 6/2011 | Escudero |
| 2012/0109171 | A1* | 5/2012 | Zeroni ........... A61B 17/320758 606/159 |
| 2013/0085514 | A1* | 4/2013 | Lee ................ A61B 17/320758 606/159 |

(Continued)

FOREIGN PATENT DOCUMENTS

EP 3222228 A1 9/2017

OTHER PUBLICATIONS

International Search Report and Written Opinion Dated Jun. 28, 2021 For International Application No. PCT/EP2021/056611 filed Mar. 16, 2021.

*Primary Examiner* — Majid Jamialahmadi (57) ABSTRACT

A thrombectomy device including a handle, a catheter and a cutting assembly at the distal end of the catheter. The thrombectomy device includes two oppositely wound helical wires, whereupon rotating in opposite direction, the helical wires cooperate to convey thrombus material form the distal end of the catheter to the proximal end of the thrombectomy device without the thrombus material adhering to the inner lumen of the catheter.

6 Claims, 7 Drawing Sheets

(56) References Cited

U.S. PATENT DOCUMENTS

| | | |
|---|---|---|
| 2018/0110540 A1 | 4/2018 | Palushi |
| 2019/0021758 A1 | 1/2019 | Nishio |
| 2019/0046230 A1 | 2/2019 | Smith |

* cited by examiner

DUAL-ACTION THROMBECTOMY CATHETER

CROSS-REFERENCE TO RELATED APPLICATION

This application is the U.S. National Phase application under 35 U.S.C. § 371 of International Application No. PCT/EP2021/056611 filed Mar. 16, 2021, which claims the benefit of U.S. Provisional Patent Application No. 62/990,488 filed Mar. 17, 2020. These applications are hereby incorporated by reference herein.

FIELD OF THE DISCLOSURE

The devices and methods described herein generally relate to the treatment of occluded body lumens, such as the removal of occlusive material, including a thrombus, from a subject's vasculature.

BACKGROUND

Various devices are used in percutaneous coronary intervention (PCI) and peripheral vascular intervention to remove thrombi, which are also referred to as blood clots. For example, certain mechanically-cutting catheters and suction catheters are currently used to remove a thrombus. Due to the characteristics of the thrombus, as it travels from the distal end of the catheter to the proximal end of the catheter, the thrombus may adhere to the internal lumen of the catheter, even in the presence of suction.

SUMMARY

What is needed is a medical device that can perform a thrombectomy and better convey a thrombus through a thrombectomy device from its distal end to its proximal end without adhering to the inner lumen of the catheter portion of the thrombectomy device. The present disclosure presents a thrombectomy system and device that achieves this goal.

An example of a thrombectomy device comprises a handle configured to be manipulated by a user; a catheter extending from the handle, a cutting assembly, wherein the cutting assembly comprises: a drive shaft having a proximal end, a distal end and an inner helical coil affixed to the drive shaft, wherein the inner helical coil is wound in a first direction; an inner cutting head coupled to the distal end of the drive shaft, wherein the inner cutting head comprises a plurality of openings, wherein each of the openings of the inner cutting head comprise a corresponding number of cutting edges; an outer helical coil radially spaced from the drive shaft and the inner helical coil, wherein the outer helical coil is wound in a second direction opposite the first direction; an outer cutting head coupled to a distal end of the second helical coil, wherein the outer cutting head comprises a plurality of openings, wherein each of the openings of the outer cutting head comprise a corresponding number of cutting edges, wherein the inner cutting head is disposed radially within the outer cutting head and rotatable relative to the outer cutting head; and an outer sheath disposed over the outer helical coil; and drive mechanism disposed within the handle, whereupon operation of the drive mechanism, the rotatable drive shaft and the inner cutting head rotate in the first direction, the outer helical coil and the outer cutting head rotate in the second direction, and the inner helical coil and the outer helical coil rotate appear to move from the distal end to the proximal end.

The thrombectomy device according to the previous paragraph, wherein the first direction is the clockwise direction.

The thrombectomy device according to any of the previous paragraphs, wherein the second direction is the counter-clockwise direction.

The thrombectomy device according to any of the previous paragraphs, wherein the inner cutting head comprises a inner blades.

The thrombectomy device according to any of the previous paragraphs, wherein the inner blade is disposed within the inner cutting head.

The thrombectomy device according to any of the previous paragraphs, wherein the inner blade is generally perpendicular to the cutting edges of the inner cutting head.

The thrombectomy device according to any of the previous paragraphs, wherein the inner blade has a curved shaped.

The thrombectomy device according to any of the previous paragraphs, wherein the curved shaped is similar to a sickle.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
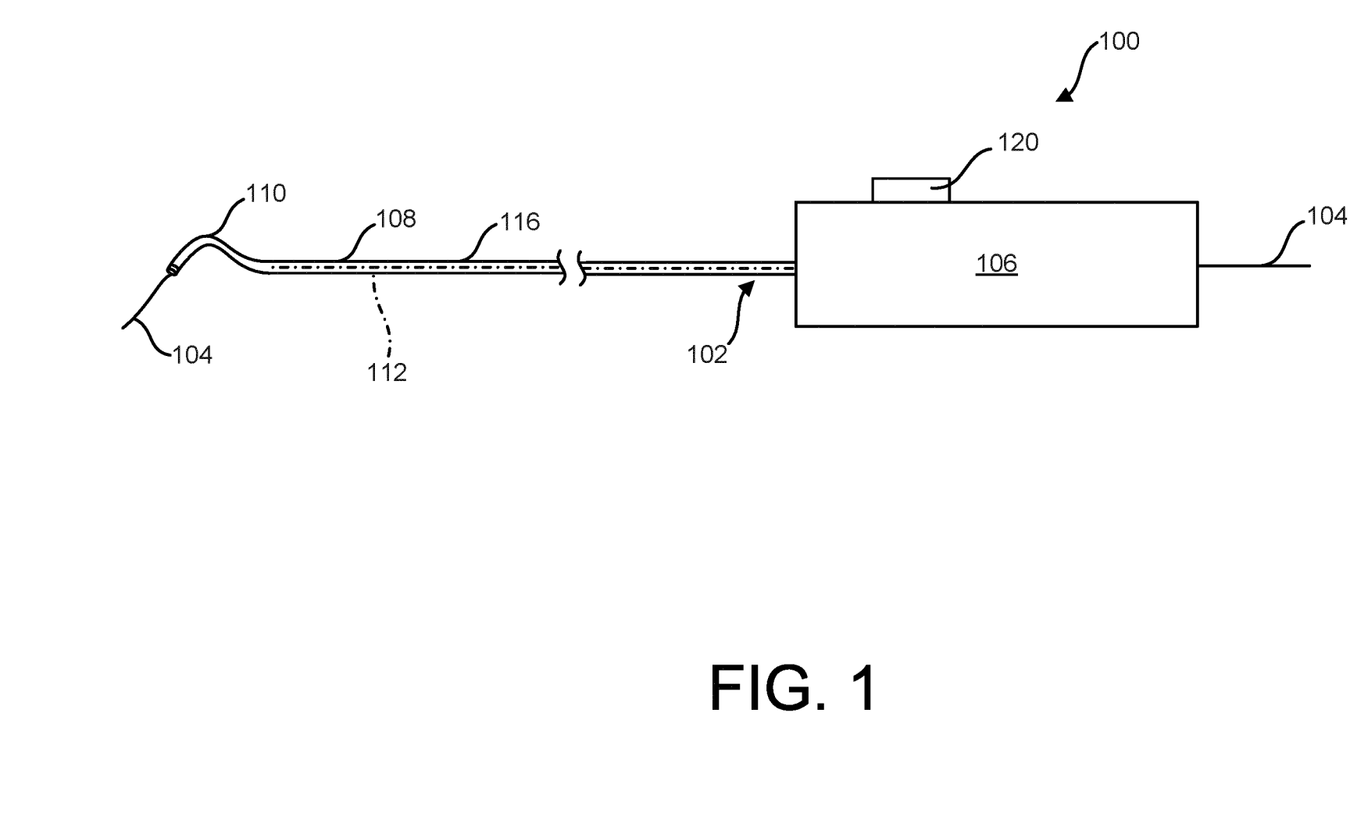
FIG. 1 is a side/schematic view of an example of a thrombectomy system according to the present disclosure.

The present disclosure relates generally to devices, systems, and methods for performing thrombectomy. Although the present disclosure primarily discusses using the devices and systems to perform a thrombectomy, the devices and systems discussed herein may be used to perform other vascular procedures, such as atherectomy. Referring to FIG. 1, there is shown an exemplary thrombectomy system 100 described herein. The thrombectomy system 100 includes an intravascular thrombectomy device 102 and a guidewire 104 over which the thrombectomy device 102 may be deployed in a subject's vasculature. In some embodiments, the guidewire 104 is silicon-coated or non-coated (bare), or otherwise free of a PTFE coating. Thrombectomy systems according to some embodiments of the present disclosure comprise a guidewire 104 that includes a PTFE coating, or atherectomy systems according to some embodiments of the present disclosure lack a guidewire.

Figure 2:
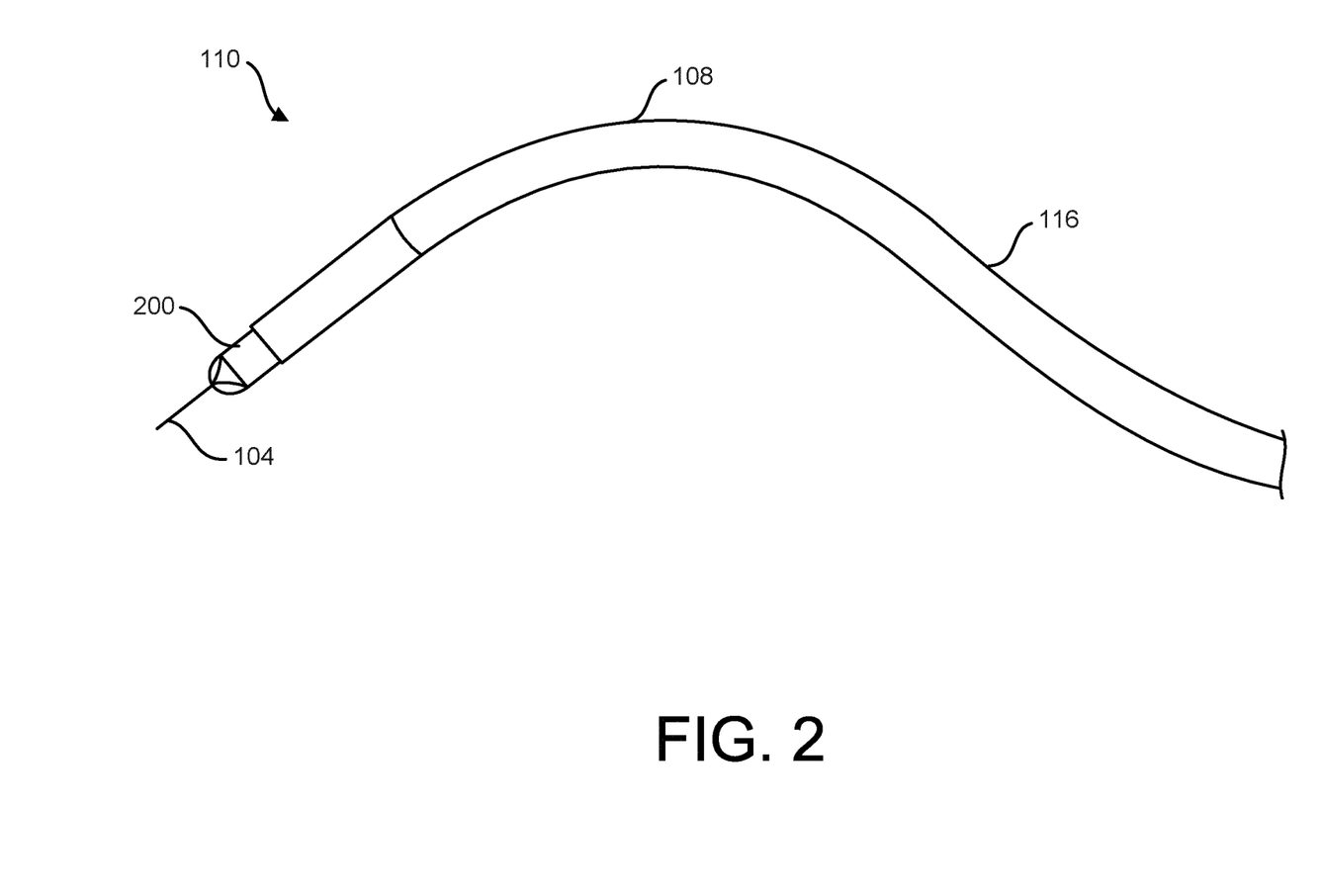
FIG. 2 is a detail side view of a distal portion of the thrombectomy device of FIG. 1.

With continued reference to FIG. 1, the thrombectomy device 102 generally includes a handle 106 and a catheter 108. The handle 106 is configured to be grasped and manipulated by a user (for example, a medical professional) during a thrombectomy procedure or other vascular procedure. The catheter 108 is coupled to and extends distally relative to the handle 106. The catheter 108 is configured to be positioned in the vasculature of a subject (for example, a patient) during an thrombectomy procedure to facilitate removal of occlusive material (for example, a thrombus) therefrom. In some embodiments and as illustrated, a distal portion 110 of the catheter 108 has a curved shape or configuration. In some embodiments, the distal portion 110 of the catheter 108 normally has a curved configuration ("normally" being understood as the catheter 108 not being subjected to any external contact forces due to, for example, contact with blood vessel walls) and may be deflected to other configurations. In other embodiments, the distal portion 110 of the catheter 108 normally has a straight shape or configuration and may be deflected to other configurations. In some embodiments, the catheter 108 is selectively rotatable about a catheter rotation axis 112 relative to the handle 106 to facilitate appropriately positioning and or "sweeping" the distal portion 110 of the catheter 108 during an atherectomy procedure. In some embodiments and as illustrated, the handle 106 carries a switch 120 for rotating the catheter 108 relative to the handle 106. Referring to FIG. 2, the catheter 108 includes an outer sheath 116, and the outer sheath 116 couples to a cutter assembly 200 that extends distally therefrom. The cutter assembly 200 is described in further detail below. Although it is not shown in the figures, the thrombectomy device 102 may also include another outer sheath that is stationary and connected to the distal end of the handle 106 to minimize vessel damage by the rotating catheter 108.

Figure 3:
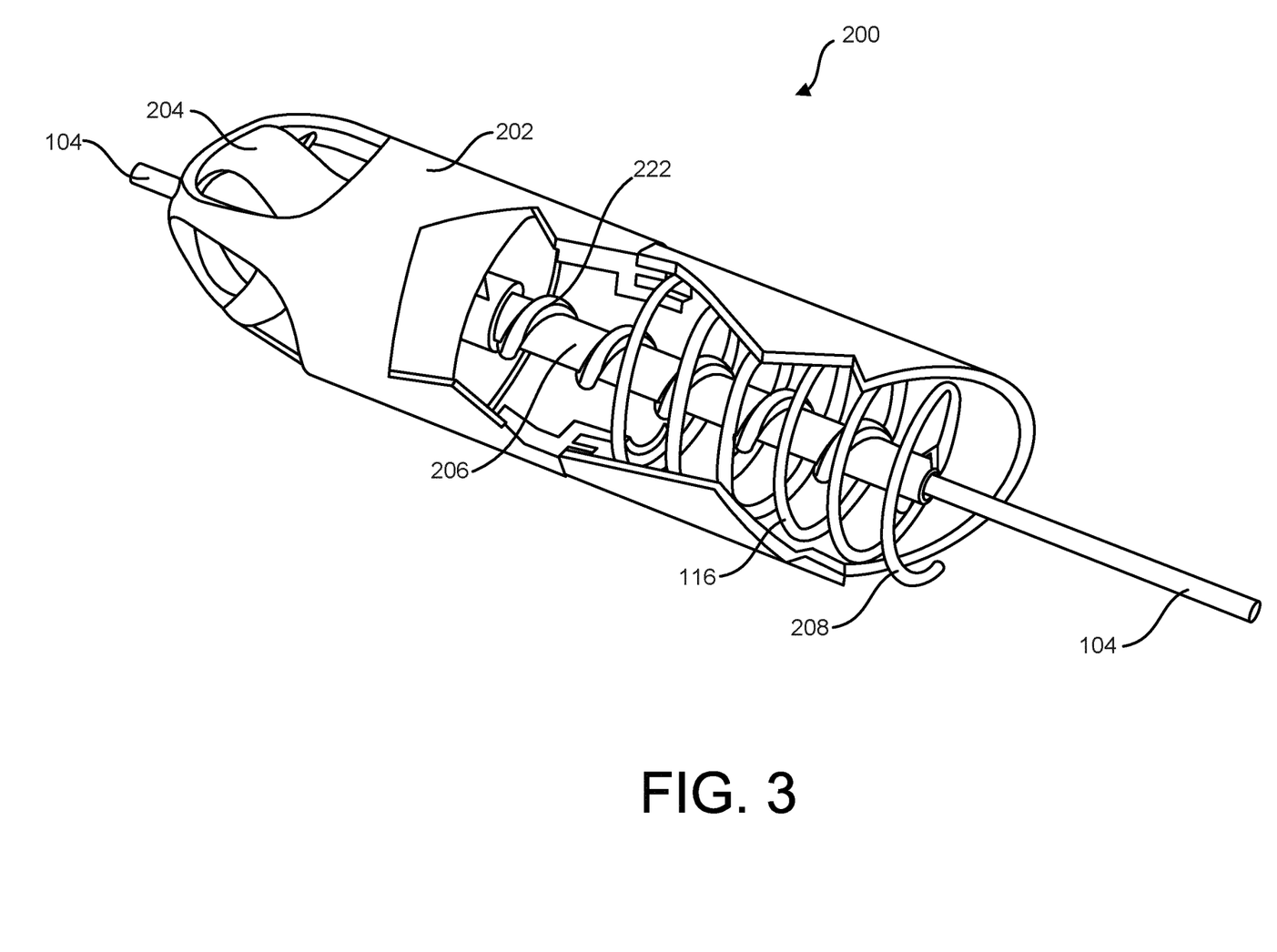
FIG. 3 is a detail perspective, cut-away view of the distal portion of the thrombectomy device of FIG. 1 the cutting assembly of the thrombectomy device.
Figure 4A:
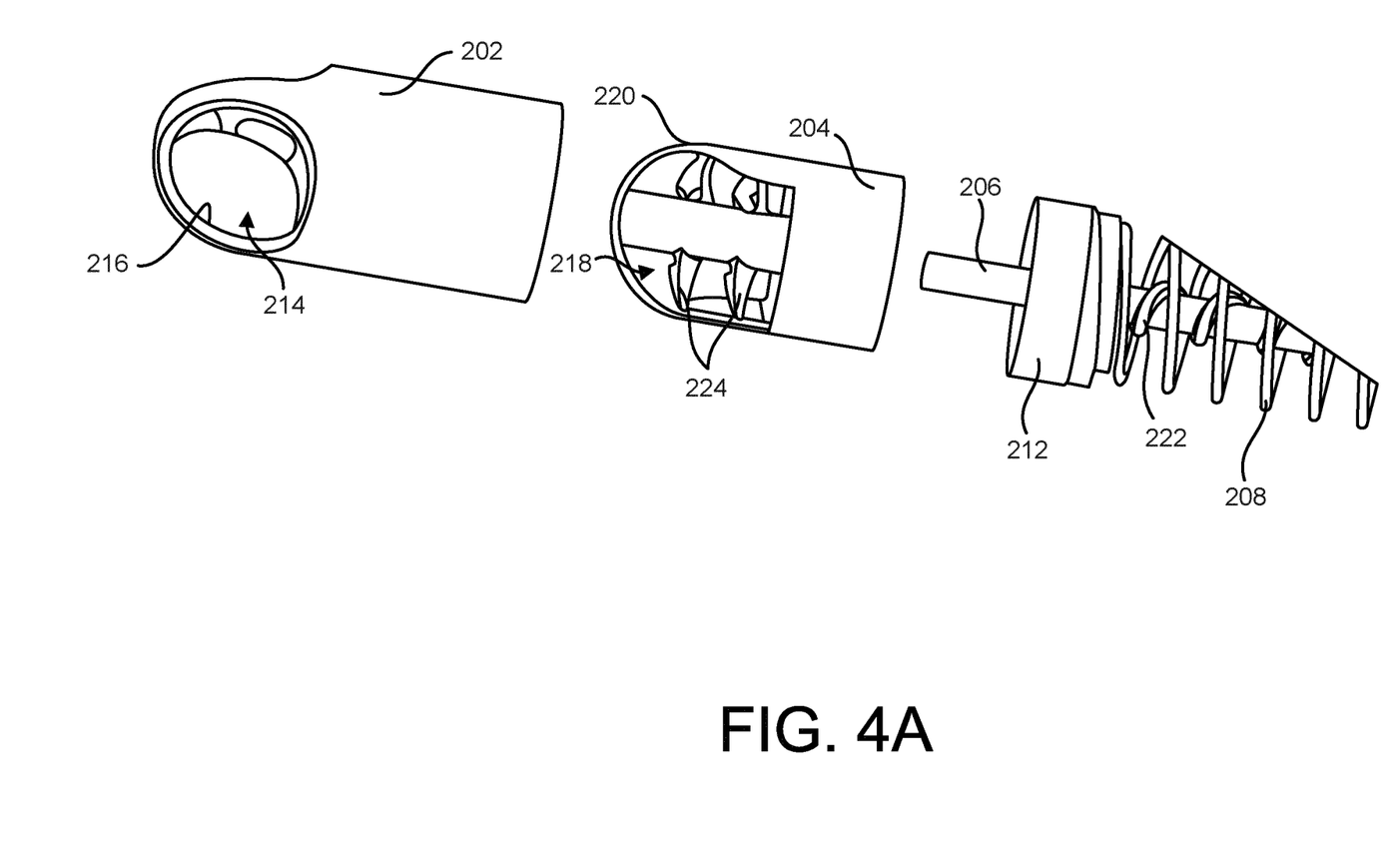
FIG. 4A is a detail perspective, exploded view of the distal portion of the thrombectomy device, particularly the cutting assembly of the thrombectomy device, of FIG. 3.
Figure 4B:
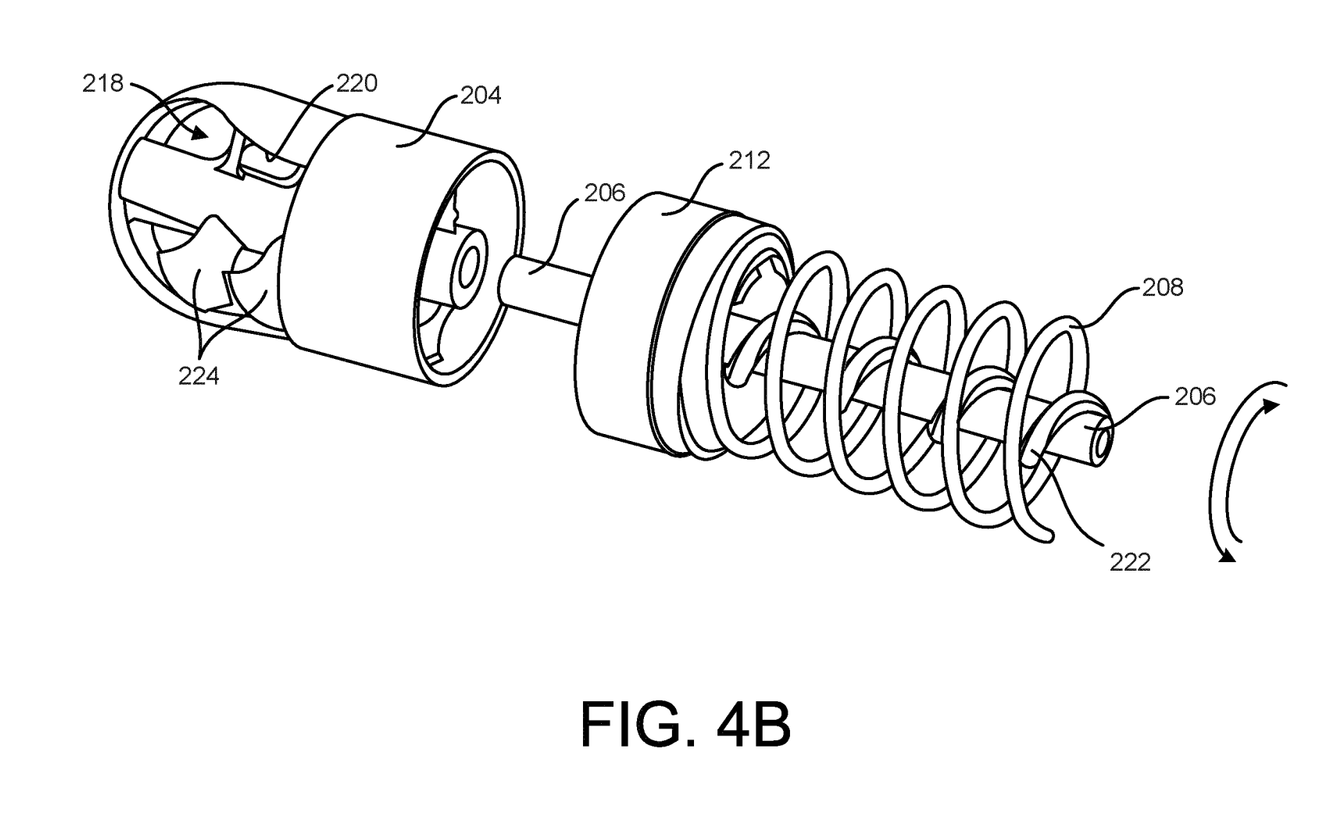
FIG. 4B is a perspective view of an inner cutting head of the thrombectomy device of FIG. 1

Referring to FIGS. 3, 4A and 4B, there is depicted the distal portion 110 of the catheter 108, including, among other components, the outer sheath 116 and the cutter assembly 200. The cutter assembly 200 includes a rotating, outer cutting head 202 and a rotating, inner cutting head 204 disposed radially concentrically within the outer cutting head 202. The outer cutting head 202 has a plurality of openings 214, and at least a portion of the outer cutting head 202 that creates the openings 214 includes a sharp cutting edge (or blade) 216. The inner cutting head 204 has a plurality of openings 218, and at least a portion of the inner cutting head 204 that creates the openings 218 includes a sharp cutting edge (or blade) 220.

It may be preferable for the number of openings 218 in the inner cutting head 204 to be the same as the number of openings 214 in the outer cutting head 202. As will be discussed in more detail below, the inner cutting head 204 will rotate in one direction, and the outer cutting head 202 will rotate in the opposite direction. For example, from the perspective of proximal end of the cutting head 200 looking in the distal direction, the inner cutting head 204 will rotate in the clockwise direction, and the outer cutting head 202 will rotate in the counter-clockwise direction. Because both the outer cutting head 202 and the inner cutting head 204 rotate in opposite directions, the respective edges 216, 220 of the cutting heads 206, 204 act like a pair of scissors and cut a thrombus within a subject's vasculature.

The inner cutting head 204 may also have one or a plurality of inner blades 224, which are disposed within the inner cutting head 204. The inner blades 224 are generally perpendicular to the sharp cutting edges (or blades) 220. After the respective edges 216, 220 of the cutting heads 206, 204 cut the thrombus, the cut portion(s) of the thrombus enters the inner cutting head 204, and the inner blades 224 rotates and chop the thrombus into smaller pieces. The inner blades 224 may be have a curved shaped similar to a sickle, and the curved sickle shape may function or act like a turbine to draw the thrombus material further inside the inner cutting head 204 and thrust such material proximally within the catheter 108. The depth of the cut by the curved shaped inner blades 224 are designed to coordinate with the speed of rotation of the outer blade 202. For example, slow rotation or stopping-starting of both the inner blades 224 and outer blades 204 and 202 respectively, causes an open window effect through which thrombus material protrudes and enters into the inner cutting head 204 for dissection. Conversely, high speed will effectively push thrombus material away from the rotating sharp edges of the cutting heads 206, 204 to minimize cutting by the inner blades 224. Therefore, depth of cut can be controlled by rotational speed. As will be made clear from the description of the drive system below, the cutting heads 206, 204 rotate at the same or substantially the same speed.

Continuing to refer to FIGS. 3, 4A and 4B, the inner cutting head 204, such as the proximal end of the inner cutting head 204 is fixedly coupled to the distal end of a rotatable drive shaft 206, which may have a lumen extending therethrough. The outer cutting head 202, such as the proximal end of the outer cutting head 202 is fixedly coupled to the distal end of a rotatable helical coil 208, which may also be referred to as the outer helical coil. Specifically, the outer cutting head 202 is coupled to the distal end of a rotatable helical coil 208 by a coupling 212. The coupling 212 has a lumen through which the rotatable drive shaft 206 passes. That is, the rotatable drive shaft 206 is configured to rotate freely relative to the coupling 212. Additionally, the rotatable drive shaft 206 rotates in one direction, and the coupling 212 rotates in the opposite direction. The helical coil 208 drives the outer cutting head 202 (and coupling 212) in one direction, and the rotatable drive shaft 206 drives the inner cutting head 204 in the opposite direction. As discussed above, the inner cutting head 204 will rotate in the clockwise direction, and the outer cutting head 202 will rotate in the counter-clockwise direction. Hence, the rotatable drive shaft 206 rotates in the clockwise direction and drives the inner cutting head 204 in the clockwise direction, and the helical coil 208 rotates in the counter-clockwise direction and rotates the outer cutting head 202 in the counter-clockwise direction.

As shown in FIGS. 3, 4A and 4B, the helical coil 208 is wound in a clockwise direction as it progresses axially from its proximal end to its distal end. The drive shaft 206 also comprises a helical coil 222, which is affixed thereto. The helical coil 222 may also be referred to as an inner helical coil. The helical coil 222 is wound in a direction opposite of the direction in which the outer helical coil 208 is wound. That is, the inner helical coil 222 is wound in a counter-clockwise direction as it progresses axially from its proximal end to its distal end. Because the rotatable drive shaft 206 and the inner cutting head 204 rotates in the clockwise direction and the inner helical coil 222 is wound in a counter-clockwise direction from its proximal end to its distal end, the inner helical coil 222 conveys thrombus material through the catheter 108 in a direction from its distal end to its proximal end because the inner helical coil 222 appears to be moving from the distal end of the catheter 108 to the proximal end of the catheter 108. And because the outer helical coil 208 and the outer cutting head 202 rotate in the counter-clockwise direction and the outer helical coil 208 is wound in a clockwise direction from its proximal end to its distal end, the outer helical coil 208 conveys thrombus material through the catheter 108 in a direction from its distal end to its proximal end because the outer helical coil 208 appears to be moving from the distal end of the catheter 108 to the proximal end of the catheter 108. That is, although the inner helical coil 222 and the outer helical coil 208 have coil wrapping configurations in opposite direction and the inner helical coil 222 and the outer helical coil 208 rotate in opposite directions, the wrappings of the inner helical coil 222 and the outer helical coil 208 cooperate and act in concert to move thrombus material through the catheter 108 in the same direction—a direction from the distal end of the catheter 108 to its proximal end—because when the wrappings of the inner helical coil 222 and the outer helical coil 208 rotate, they pull and propagate thrombus material in the same direction (i.e., from the distal end to the proximal end of the catheter 108). Because the wrappings of the inner helical coil 222 and the outer helical coil 208 cooperate and act in concert to move thrombus material through the catheter 108 in the same direction in the thrombectomy device 102 convey a thrombus through the catheter 108 from a distal end of the device to the proximal end of the device without adhering to the inner lumen of the catheter 108. Although not shown in any of the figures, the thrombectomy system 100 and/or the thrombectomy device 102 may be configured to provide suction to the catheter 108 to further enhance the conveyance of thrombus. Additionally, saline, drugs, and other liquids may be injected distally through ports or holes drilled radially through the drive shaft 206 to allow liquid to migrate from within the hollow drive shaft 206 into the catheter space to suspend and/or lubricate and/or dissolve the thrombus suspending it for improved movement proximally towards the handle where optional suction may assist the removal of the thrombus material.

Figure 5A:
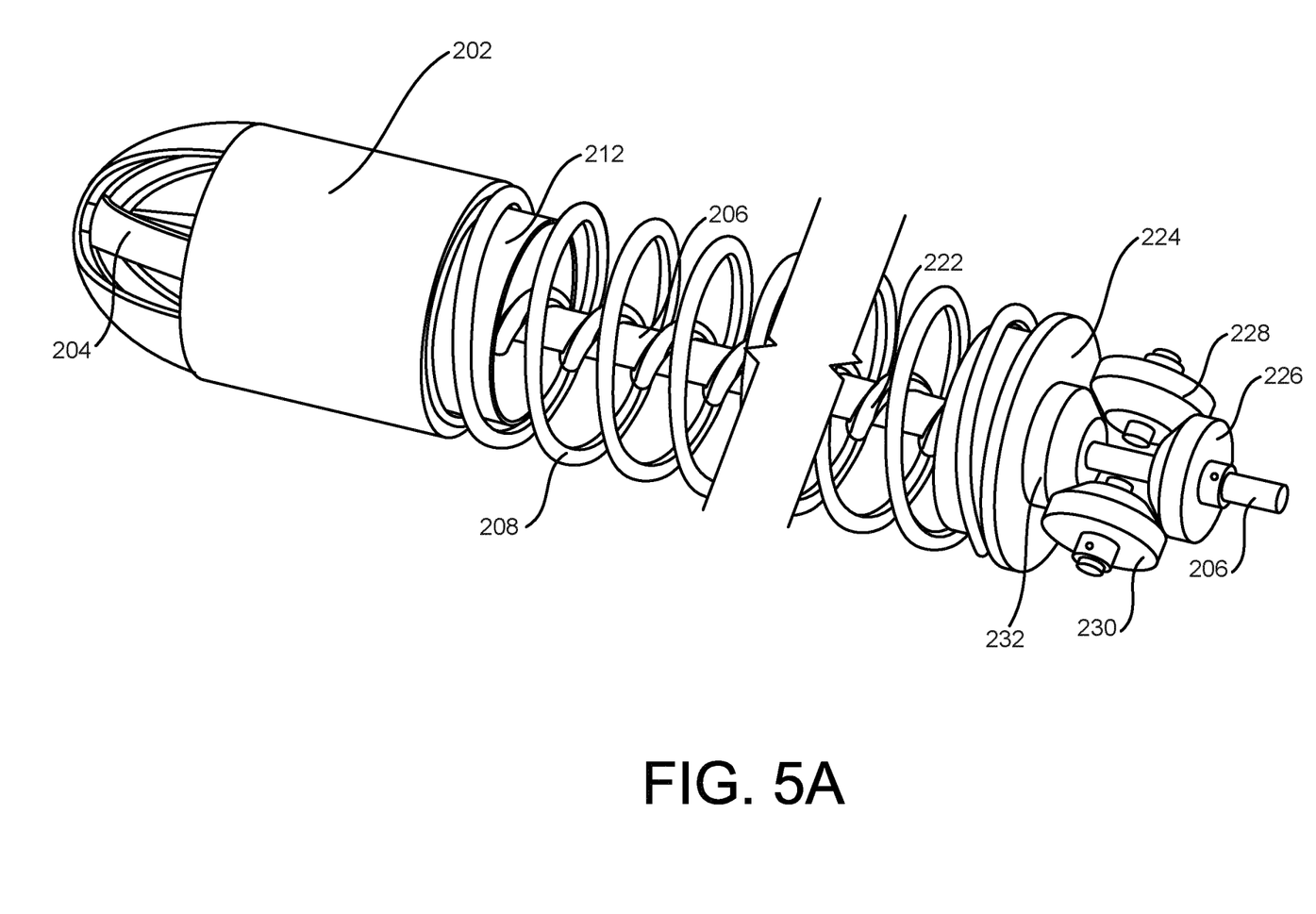
FIG. 5A is a perspective view of a distal portion and proximal portion of a thrombectomy device, including the cutting assembly and a drive system coupled to the inner cutting head and outer cutting head according to an example of the present disclosure.
Figure 5B:
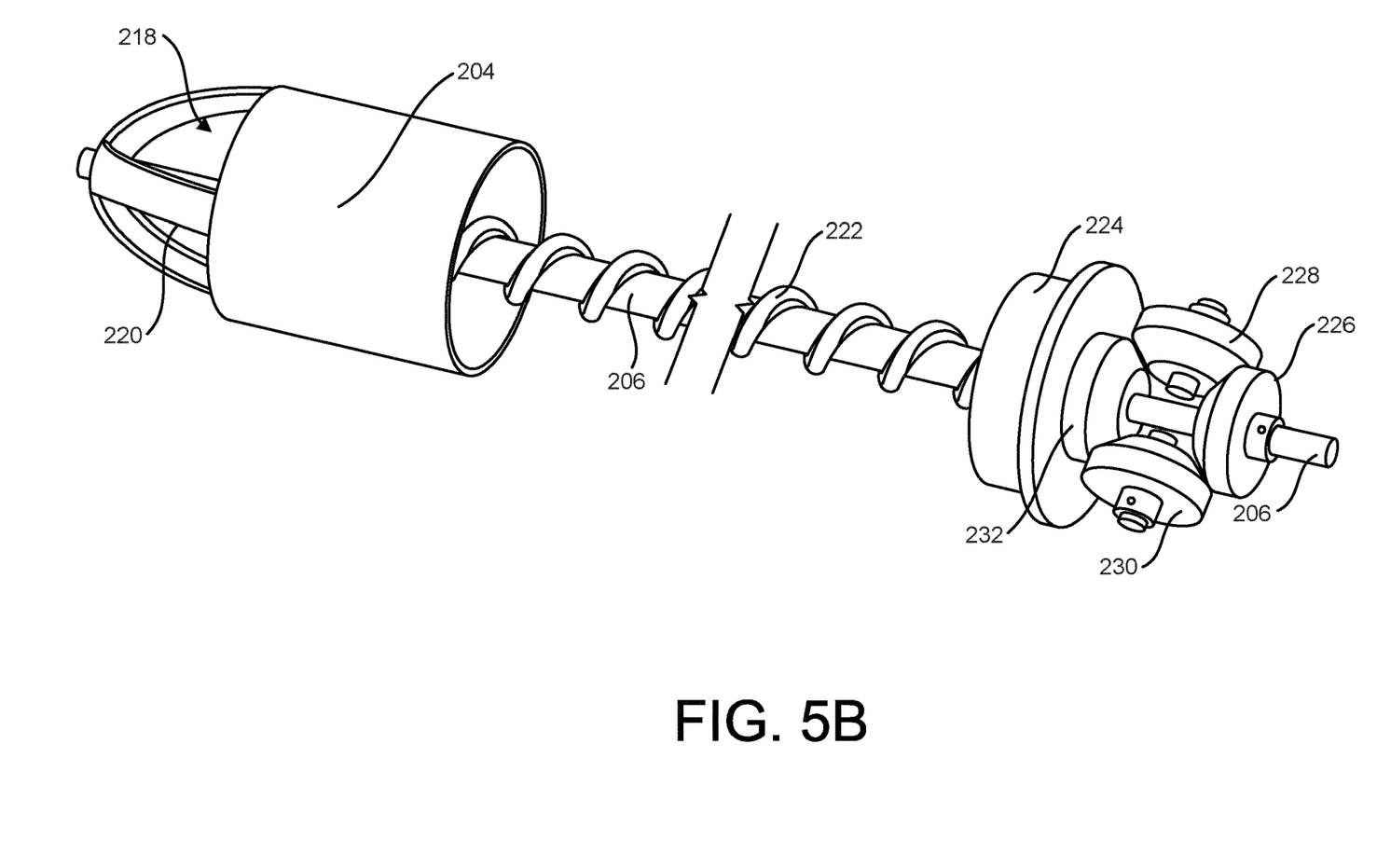
FIG. 5B is a perspective view of the inner cutting head and the drive system coupled to the inner cutting head according to an example of the present disclosure.

Referring to FIGS. 5A and 5B, there is depicted is a mean for driving and rotating the rotatable drive shaft 206 rotates in one direction, and helical coil 208 in the opposite direction. The drive means may be disposed within the handle 106 of the thrombectomy device 102 and include a set of planetary gears, wherein a distal gear 226 is fixedly coupled to the drive shaft 206, which in turn is fixedly coupled to a motor (not shown). Because the distal gear 226 is fixedly coupled to the drive shaft 206, upon a user activating the switch 120, which is electrically coupled to the motor, the motor rotates the distal gear 226 and the drive shaft 206 in the clockwise direction. Two planetary gears 228, 230 couple the planetary proximal gear 226 to the planetary distal gear 232 and are configured to rotate the planetary proximal gear 232 in a direction opposite (i.e., counter-clockwise direction) that of the planetary distal gear 226. The planetary distal gear 232 is coupled to the outer helical coil 208 via a coupling 224, which may be a separate component or integral with the planetary distal gear 232. Similar to coupling 212, the drive shaft 206 passes through a lumen in the coupling 224 and/or the planetary distal gear 232, and the drive shaft 206 rotates in one direction opposite that the coupling 224 rotates.

The foregoing discussion has been presented for purposes of illustration and description. The foregoing is not intended to limit the disclosure to the form or forms disclosed herein. For example, the lumen in the drive shaft 206 allows for numerous devices to pass therethrough, such as a guidewire, ultrasound catheter, vision system, an expanding umbrella mesh for catching debris, as well as fluid or medication delivery.

In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A thrombectomy device, comprising:
    a handle configured to be manipulated by a user;
    a catheter extending from the handle,
    a cutting assembly, wherein the cutting assembly comprises:
        a drive shaft having a proximal end, a distal end and an inner helical coil affixed to the drive shaft, wherein the inner helical coil is wound in a first direction;
        an inner cutting head coupled to the distal end of the drive shaft, wherein the inner cutting head comprises a plurality of openings, wherein each of the openings of the inner cutting head comprise a corresponding number of cutting edges;
        an outer helical coil radially spaced from the drive shaft and the inner helical coil, wherein the outer helical coil is wound in a second direction opposite the first direction;
        an outer cutting head coupled to a distal end of the outer helical coil, wherein the outer cutting head comprises a plurality of openings, wherein each of the openings of the outer cutting head comprise a corresponding number of cutting edges, wherein the inner cutting head is disposed radially within the outer cutting head and rotatable relative to the outer cutting head; and
        an outer sheath disposed over the outer helical coil; and
    a drive mechanism disposed within the handle, whereupon operation of the drive mechanism, the drive shaft and the inner cutting head rotate in the first direction, the outer helical coil and the outer cutting head rotate in the second direction, and the inner helical coil and the outer helical coil rotate to appear to move from the distal end to the proximal end;
    wherein the inner cutting head comprises an inner blade and the inner blade is disposed within the inner cutting head.

2. The thrombectomy device of claim 1, wherein the first direction is the clockwise direction.

3. The thrombectomy device of claim 2, wherein the second direction is the counter-clockwise direction.

4. The thrombectomy device of claim 1, wherein the inner blade is generally perpendicular to the cutting edges of the inner cutting head.

5. The thrombectomy device of claim 4, wherein the inner blade has a curved shaped.

6. The thrombectomy device of claim 5, wherein the curved shaped is similar to a sickle.

\* \* \* \* \*